(12) United States Patent
Young et al.

(10) Patent No.: US 11,504,013 B1
(45) Date of Patent: Nov. 22, 2022

(54) SYSTEMS AND METHODS FOR BLOOD PRESSURE MEASUREMENTS

(71) Applicant: Apple Inc., Cupertino, CA (US)

(72) Inventors: Derek Young, Fremont, CA (US); Alexander M. Chan, Sunnyvale, CA (US); German A. Alvarez, San Jose, CA (US); Joseph R. Lee, Belmont, CA (US); Manda Paul, Sunnyvale, CA (US); Santiago M. Quijano, San Jose, CA (US)

(73) Assignee: Apple Inc., Cupertino, CA (US)

( * ) Notice: Subject to any disclaimer, the term of this patent is extended or adjusted under 35 U.S.C. 154(b) by 398 days.

(21) Appl. No.: 16/439,586

(22) Filed: Jun. 12, 2019

Related U.S. Application Data

(60) Provisional application No. 62/684,081, filed on Jun. 12, 2018.

(51) Int. Cl.
*A61B 5/022* (2006.01)
*A61B 5/01* (2006.01)
(Continued)

(52) U.S. Cl.
CPC ........ *A61B 5/02225* (2013.01); *A61B 5/0024* (2013.01); *A61B 5/01* (2013.01);
(Continued)

(58) Field of Classification Search
CPC .... A61B 2562/0219; A61B 2562/0247; A61B 5/0024; A61B 5/0077; A61B 5/01;
(Continued)

(56) References Cited

U.S. PATENT DOCUMENTS

| | | | |
|---|---|---|---|
| 2005/0054940 A1* | 3/2005 | Almen | A61B 5/4809 600/509 |
| 2013/0060147 A1* | 3/2013 | Welch | A61B 5/02208 600/479 |

(Continued)

FOREIGN PATENT DOCUMENTS

WO   WO-2014047310 A1 *   3/2014   ............... A61B 5/05

*Primary Examiner* — Sean P Dougherty
*Assistant Examiner* — Alexander H Connor
(74) *Attorney, Agent, or Firm* — Brownstein Hyatt Farber Schreck, LLP

(57) ABSTRACT

A monitoring system configured to measure the user's health-related parameters while in a certain state is disclosed. Based on whether the user is in the certain state and/or one or more criteria being met, the monitoring system can perform a physiological measurement such as a blood pressure measurement. The monitoring system can be capable of dynamically adjusting the measurement parameters, criteria, and acquired information based one or more scalers. The criteria can be based on user states or conditions such that user disruptions can be reduced and the measurement accuracy and/or efficiency can be enhanced. The monitoring system can also measure the user's parameters during the measurement and may abort the measurement if the measurement may not have accurate information and/or to reduce any disruption to the user. Alternatively, the measurement can be annotated so that the measurement can be used during data interpretation with certain qualifiers attached.

20 Claims, 6 Drawing Sheets

(51) Int. Cl.
    *A61B 5/024*     (2006.01)
    *A61B 5/00*     (2006.01)
    *A61B 5/11*     (2006.01)

(52) U.S. Cl.
    CPC ...... *A61B 5/02233* (2013.01); *A61B 5/02405* (2013.01); *A61B 5/1116* (2013.01); *A61B 5/6824* (2013.01); *A61B 5/0077* (2013.01); *A61B 5/02438* (2013.01); *A61B 5/1113* (2013.01); *A61B 5/4809* (2013.01); *A61B 5/6828* (2013.01); *A61B 5/6892* (2013.01); *A61B 5/7207* (2013.01); *A61B 2562/0219* (2013.01); *A61B 2562/0247* (2013.01)

(58) Field of Classification Search
    CPC ............ A61B 5/02225; A61B 5/02233; A61B 5/02405; A61B 5/02438; A61B 5/1113; A61B 5/1116; A61B 5/4809; A61B 5/6824; A61B 5/6828; A61B 5/68892; A61B 5/7207

See application file for complete search history.

(56) References Cited

U.S. PATENT DOCUMENTS

| | | | |
|---|---|---|---|
| 2013/0226010 A1* | 8/2013 | Hotta | A61B 5/025 600/490 |
| 2013/0296723 A1* | 11/2013 | Cho | A61B 5/02108 600/501 |
| 2015/0282768 A1* | 10/2015 | Luna | A61B 5/0205 600/386 |
| 2015/0305689 A1* | 10/2015 | Gourmelon | G16H 50/20 600/301 |
| 2018/0192946 A1* | 7/2018 | Adachi | A61B 5/022 |
| 2018/0220900 A1* | 8/2018 | Meng | A61B 5/1118 |
| 2019/0380580 A1* | 12/2019 | Kitagawa | A61B 5/7207 |

* cited by examiner

SYSTEMS AND METHODS FOR BLOOD PRESSURE MEASUREMENTS

CROSS-REFERENCE TO RELATED APPLICATION

This application claims the benefit under 35 U.S.C. § 119(e) of U.S. Provisional Patent Application No. 62/684,081, filed Jun. 12, 2018; the content of which is incorporated by reference herein in its entirety for all intended purposes.

FIELD OF THE DISCLOSURE

This disclosure relates to systems and methods for tracking of health conditions. More particularly, this disclosure relates to monitoring systems and methods for taking a cuff-based measurement of a user's blood pressure and/or other health metrics during sleep or during other user states.

BACKGROUND OF THE DISCLOSURE

Blood pressure measurements can be used to determine a user's health conditions. Performing frequent blood pressure measurements and tracking the measurements can help detect certain health conditions (e.g., cardiovascular disease, cardiovascular mortality, target organ damage, etc.) and assist in determining the effectiveness of a prescribed treatment. In some instances, detecting the health condition can be more accurate when the blood pressure measurement is taken while the user is sleeping. One way to measure the user's blood pressure is to use an ambulatory blood pressure monitor (ABPM), which may include a cuff that inflates to occlude blood flow in the user's arm, for example. In some occurrences, such as with a monitoring system that inflates the cuff at predetermined intervals, inflation may disrupt the user's sleep and/or the sleep of the user's partner. It may be desirable for the monitoring system to dynamically inflate the cuff and perform blood pressure measurements based on one or more criteria being met.

SUMMARY OF THE DISCLOSURE

Disclosed herein is a monitoring system configured to take a cuff-based measurement of the user's blood pressure and/or other health metrics while the user is in a certain sleep state, or in other user states. The monitoring system can include one or more sensors configured to measure the user's parameter(s) while lying in bed and/or sleeping, or while in other user states or conditions, such as in a particular posture. The user's parameter(s) can be used to determine whether the user is in a certain state. Based on whether the user is in the certain state and/or one or more criteria being met, the monitoring system can perform a physiological measurement such as a blood pressure measurement. The monitoring system can be capable of dynamically adjusting the measurement parameters, criteria, and acquired information based one or more scalers such as the user's parameters. The criteria can be based on user states or conditions (e.g., the user's sleep state, posture, the number of successful measurements, etc.) such that user disruptions such as sleep disruption can be reduced and the measurement accuracy and/or efficiency can be enhanced, as discussed in detail below. The monitoring system can also measure the user's parameters during the measurement and may abort the measurement and/or inflation of the cuff if the measurement may not have accurate information and/or to reduce any disruption to the user. Alternatively, instead of aborting the measurement, the measurement can be annotated so that the measurement can be used during data interpretation with certain qualifiers attached.

DETAILED DESCRIPTION

Figure 1A:
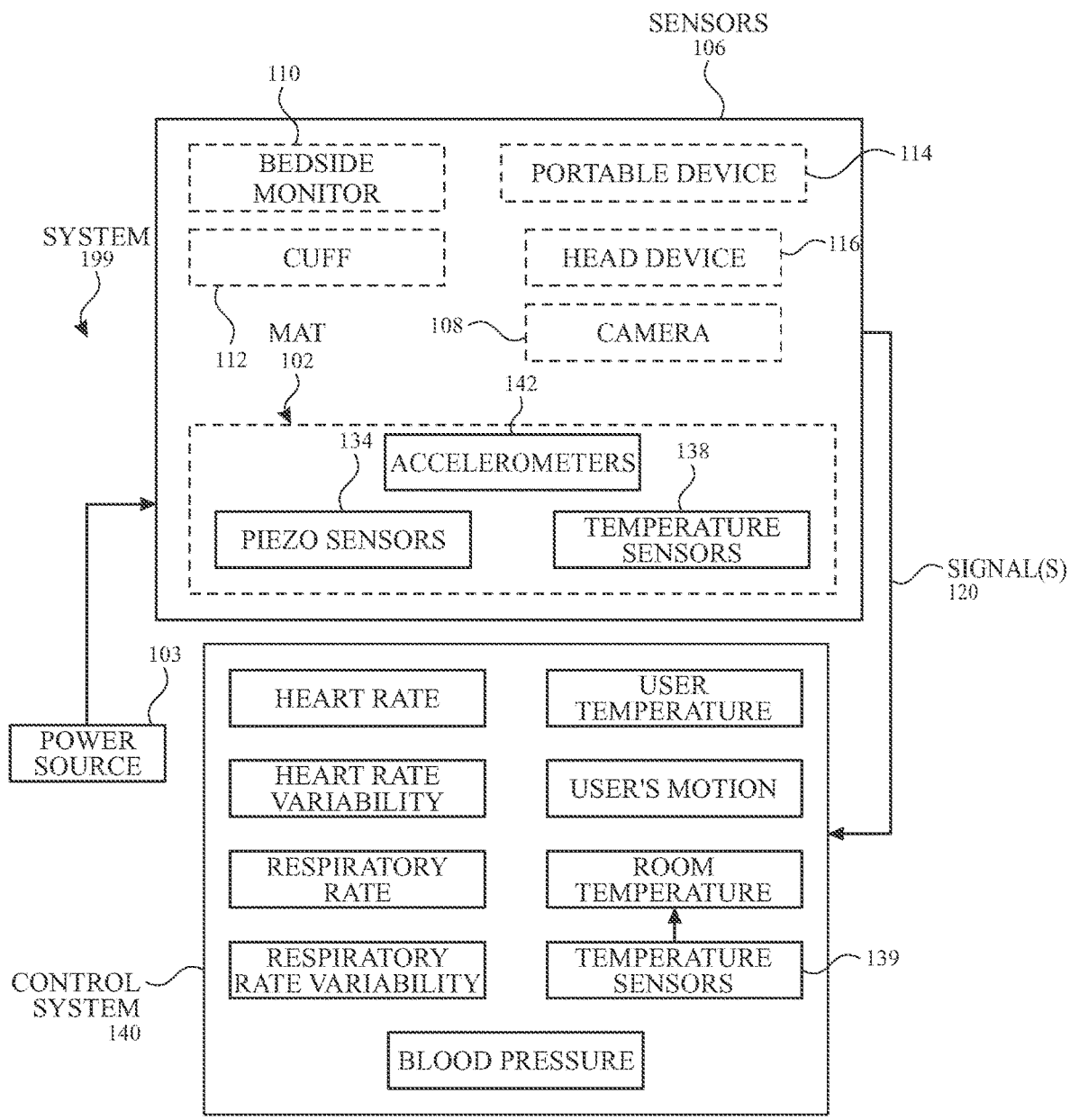
FIG. 1A illustrates a block diagram of an exemplary monitoring system according to examples of the disclosure.

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples, as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

Disclosed herein is a monitoring system configured to measure the user's blood pressure and/or other health metrics while the user is in a certain state, and methods for operating the monitoring system. Physiological measurements such as blood pressure measurements can be used to determine a user's health conditions. Performing frequent physiological measurements and tracking the measurements can help predict and/or detect certain health conditions (e.g., cardiovascular disease, cardiovascular mortality, target organ damage, etc.) and assist in determining the effectiveness of a prescribed treatment. In some instances, detecting the health condition can be more accurate when the physiological measurement such as a blood pressure measurement is taken while the user is sleeping or in some other state or condition. One way to measure the user's blood pressure is to use an ambulatory blood pressure monitor (ABPM), which may include a cuff that inflates to occlude blood flow in the user's arm, for example. In some occurrences, such as with a monitoring system that inflates the cuff at predetermined intervals, inflation may disrupt the user, and in instances where the user is asleep, the sleep of the user's partner. It may be desirable for the monitoring system to dynamically inflate the cuff and perform physiological measurements based on one or more criteria being met. The criteria can be based on various states or conditions (e.g., the user's sleep state, the number of successful measurements, etc.) such that user disruption can be reduced and the measurement accuracy and/or efficiency can be enhanced, as discussed in detail below.

Although examples of the disclosure provided below and in the figures may at times refer only to the measuring of a user's blood pressure for convenience, it should be understood that the disclosure is not so limited, but is inclusive of other physiological measurements or health metrics, referred to collectively herein as physiological measurements. In one example, the raw pressure waveform may be measured to extract other health metrics (such as the augmentation index (AIx), a measure of systemic arterial stiffness) during cuff inflation.

Additionally, examples of the disclosure can be applicable to other types of inflation-based measurements not explicitly disclosed herein. One non-limiting exemplary type of inflation-based measurement can be a partial measurement. The partial measurement may include inflating the cuff up to a certain pre-determined point, for example. The point may be based on an amount of inflation, a time for inflation, and the like. The system may use machine learning or stored information to estimate information.

Furthermore, although the examples of the disclosure provided below may refer to a user's sleep state for convenience, the disclosure is not so limited, but is inclusive of other states such as a user's posture.

Monitoring System

Figure 1B:
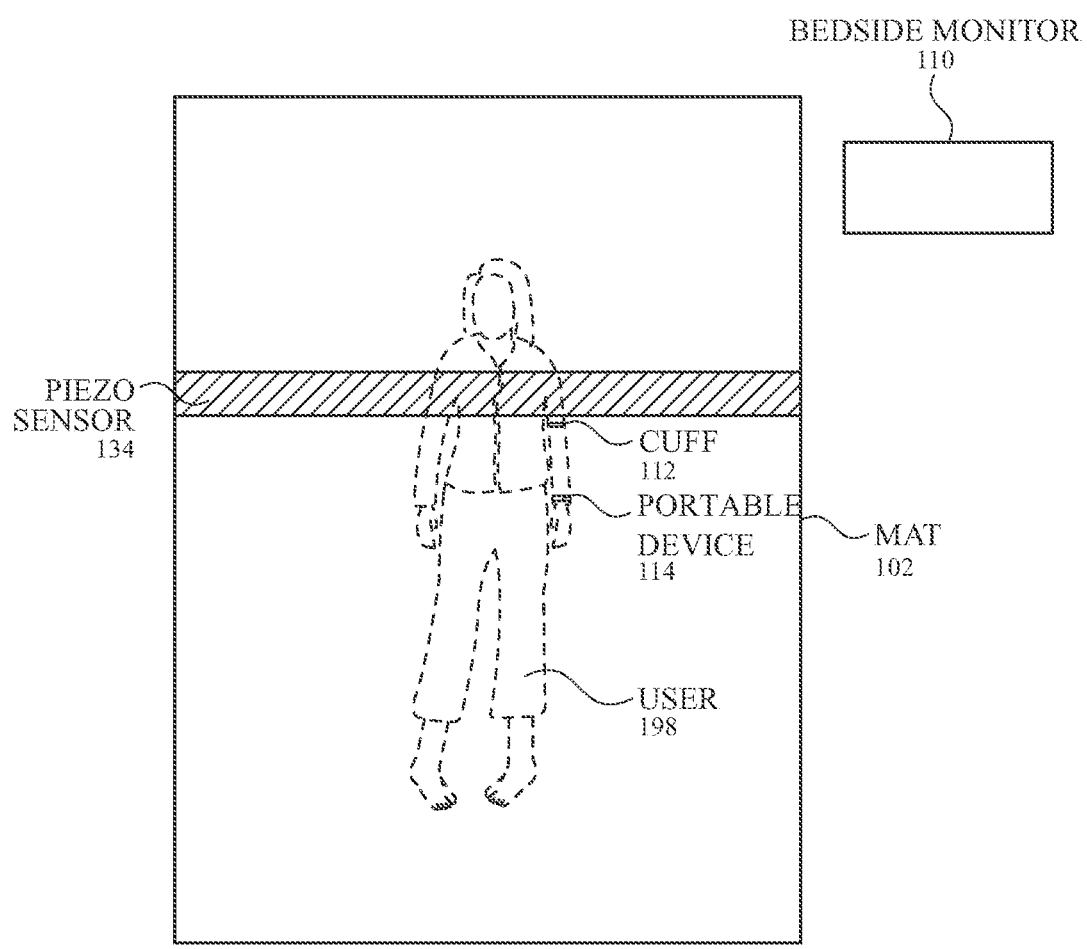
FIG. 1B illustrates a top view of an exemplary monitoring system according to examples of the disclosure.

An exemplary monitoring system and included components will now be described. FIG. 1A illustrates a block diagram of an exemplary monitoring system according to examples of the disclosure. FIG. 1B illustrates a top view of an exemplary monitoring system according to examples of the disclosure. System 199 can include sensors 106, power source 103, and control system 140. The sensors 106 can include multiple types of sensors including, but not limited to, a mat 102, a camera 108, a bedside monitor 110, a cuff 112, a portable device 114, and a head device 116.

The mat 102 can be resting on, attached to, or in contact with a bed (not shown), for example. Additionally or alternatively, the mat 102 can be configured to contact one or more human users, one or more pets, or the like. That is, the mat can be in direct contact with the human(s)/pet(s), or the mat can be in contact with one or more intermediate layers, which directly contact the human(s)/pet(s). For example, the mat 102 can be included in the user's clothing and can be configured for physiological measurements when the clothing is worn by the user. Mat 102 can be configured to cover all or a portion of a mattress, for example, which can be resting on, attached to, or supported by one or more frames of the bed. In some examples, mat 102 can be flexible. In some examples, mat 102 can be at least partially rigid. Mat 102 can include one or more of a sheet, blanket, duvet, pillow, pillowcase, or insert. Mat 102 can be a stand-alone unit that can be placed on a bed and can be incorporated into the fabric or textile used as part of a sleeping/resting arrangement. Mat 102 can include one or more sensors such as piezo sensors 134, temperature sensors 138, and accelerometers 142. The sensors can include one or more functionalities such as measuring the user's respiration rate and/or heart rate to determine, alone or in combination with signals from other components, the user's state. Although FIGS. 1A-1B illustrate mat 102 as including three different types of sensors, examples of the disclosure can include a monitoring system that includes fewer or more sensors and/or different types of sensors (e.g., electrodes configured for impedance cardiograph (ICG), electrocardiogram (ECG), and/or ballistocardiograph (BCG) measurements).

The camera 108 can be an optional device, such as a video camera, configured to perform one or more functionalities, including, but not limited to, determining the position of the user's body, determining the location of the user's body, determining the temperature of the user's body, and determining the temperature of the local ambient. The monitoring system can be configured to utilize the information from camera 108 in conjunction with the information from the one or more sensors (e.g., piezo sensors) for physiological measurements (e.g., heart rate measurements), analysis (e.g., sleep analysis), and feedback.

The bedside monitor 110 can be an optional device that is located proximate to the user (e.g., sleeping on the mat 102). The bedside monitor 110 can include one or more sensors such as a microphone (not shown) to record the user's snoring pattern. One or more signals 120 indicative of the user's snoring pattern can be transmitted to the control system 140, for example. The signals from the bedside monitor can be used with other signals to determine one or more sleep parameters, such as the sleep state of the user. In some examples, one or more functionalities and/or components of the bedside monitor 110 can be integrated with the one or more functionalities and/or components of the control system 140. For example, the control system 140 can be a bedside monitor that includes temperature sensors 139 and the microphone. Additionally or alternatively, the bedside monitor 110 can include a radar (not shown) for measuring respiration phase information.

The bedside monitor 110 can communicate with one or more other components included in the system 199 through wired or wireless (e.g., local area network) communication means. In some examples, the bedside monitor 110 can include a transceiver to receive information and a controller (or processor) to process the information for analysis (e.g., to determine the user's snore pattern). The bedside monitor 110 can compile the user's snore pattern and send the information at pre-determined intervals or once a certain amount or type of information is detected. For example, to save power, the bedside monitor 110 may not transmit any information to the control system 140 until a certain snore pattern is detected. The bedside monitor 110 may include memory configured to store pre-determined snore patterns to be compared to the measured snore pattern. If the measured snore pattern matches one of the pre-determined snore patterns, the bedside monitor may send the measured store pattern or may send a signal indicative of the match to the control system 140. Alternatively, the control system 140 may store pre-determined snore patterns and determine whether the measured snore pattern matches a pre-determined snore pattern.

The cuff 112 can be another optional device that can be located proximate to the user. In some examples, the cuff 112 can be wrapped around the user (e.g., the user's arm) while the user is sleeping, as shown in FIG. 1B. The cuff 112 can include one or more components such as a pump (not shown) and a pressure sensor (not shown). The pump can inflate the cuff 112 to cause blood flow to occlude in the user's arm. The pressure sensor can measure the amount of pressure applied by the cuff 112 to control the amount of inflation. The cuff 112 may also include one or more motion sensors (e.g., accelerometer, gyrometer, etc.) to determine the user's motion and/or the position of the body part the cuff is located proximate to. The cuff can be used along with another component, such as the mat 102, to determine the positions of the user's arm(s), leg(s), and other parts of the body and/or the user's posture.

Additionally or alternatively, the cuff 112 can include one or more optical sensors, such as a PPG or $SpO_2$ sensing unit, to determine the user's physiological information (e.g., the user's heart rate, heart rate variability, etc.). In some instances, the optical sensors can be used to measure the user's respiration and/or respiration rate variability. In some examples, the cuff 112 may include temperature sensors. The motion sensors, optical sensors, and/or temperature sensors can be used to determine changes in the user's physiological information (e.g., increased skin perfusion) that may be associated with sleep onset.

In some examples, the cuff 112 may include logic to control the inflation and the measurement parameters, such as when to start and stop the measurement, how often to measure, how long to measure, and when to abort or annotate the measurement. In other examples, the cuff 112 may receive a control signal from another component such as the control system 140 and may respond accordingly to the signal.

The portable device 114 can be an optional device that can be located proximate to the user. Exemplary portable devices include, but are not limited to, a watch, a phone, a tablet computer, a cuff, and the like. The portable device 114 can include one or more sensors such as optical sensors (e.g., PPG or $SpO_2$ sensing units) to determine the user's physiological information (e.g., the user's heart rate, heart rate variability, user's temperature, etc.). Additionally or alternatively, the optical sensors can be used to measure the user's respiration and/or respiration rate variability. The information from the optical sensors can be analyzed discretely or in conjunction with one or more other components (e.g., the mat 102, the cuff 112, etc.) to determine the user's heart rate, heart rate variability, respiration, and/or respiration rate variability. In some examples, the portable device 114 can include one or more electrodes to determine the user's ECG and/or EMG signals. In some examples, the portable device 114 can act as the control system for the monitoring system.

In some configurations, the user 198 (or a doctor, for example) can input information into the portable device 114, where the information may be used to adjust or set certain parameters, such as relaxing the measurement criteria. The portable device 114 can also display information to the user, such as results from the measurements taken during the last sleep period or recommendations on how to improve the measurement accuracy.

In some examples, the portable device 114 can include a microphone whose signals can be analyzed discretely or in conjunction with one or more other components (e.g., the bedside monitor 110, the cuff 112, etc.) to determine the user's snore pattern. Additionally or alternatively, the portable device 114 can include one or more motion sensors, such as an accelerometer, to determine the user's body movement, position, and/or posture of the user during sleep. The motion sensor information from the portable device 114 can be analyzed discretely or in conjunction with one or more other components (e.g., the mat 102, the cuff 112, etc.) to determine the user's body movement, position, and/or posture of the user.

The portable device 114 can transmit one or more signal(s) indicative of the determined physiological information to the control system 140, for example. The signals can be used with signals from other components to determine one or more sleep parameters, such as the sleep state of the user. In some examples, the portable device 114 can receive signals from other components and can include logic to analyze the signals. In some examples, the portable device 114 can be used to detect sleep apnea. The portable device 114 can communicate with one or more other components included in the system 199 through wired or wireless (e.g., local area network) communication means. In some examples, the portable device 114 can include a transceiver to receive information and a controller (or processor) to process the information for analysis (e.g., to determine the user's heart rate variability). The portable device 114 can compile the user's physiological information and send the information at pre-determined intervals or once a certain amount or type of information is detected.

The head device 116 can be another optional device that is located proximate to the user. Exemplary head devices can include, but are not limited to, a sleep mask, a hat, a headband, and the like. The head device 116 can include one or more sensors such as ECG sensors to determine the user's electrical signals (e.g., brain signals such as EEG signals). The head device 116 can transmit one or more signal(s) indicative of the user's electrical signals to the control system 140, for example. In some examples, the head device 116 can be a sleep mask that monitors the user's eye movements, which can be used to determine the user's eye movement signals (EOG) and sleep state. The signals can be used with other signals or information (e.g., the user's respiration rate) to determine one or more sleep parameters.

The power source 103 can be configured to provide power to the sensors 106 and/or control system 140. In some examples, the power source 103 can be coupled to a power outlet. In some examples, the power source 103 can be coupled to a battery and a charging station or power supply. In some examples, the power source 103 can be configured to receive power from a charging element, such as a magnetic puck. In some examples, the charging element can include an inductive coil, and power can be transferred to system 199 via an electromagnetic field.

The control system 140 can include logic configured to perform one or more functions such as communicating information to/from the sensors 106, controlling one or more parameters, analyzing one or more signals, determining one or more measurement parameters, and storing information. For example, the control system 140 can include temperature sensors 139, which can measure and provide information to the control system 140 about the temperature of the room that system 199 is located in. In some examples, the control system 140 can be configured to communicate with the mat 102 through wired (e.g., using a cable) or wireless communications. The control panel 140 can include a touch panel and/or a display and can be configured to interface with the user and/or a computer. For example, the control panel 140 can display heart rate, heart rate variability, respiratory rate, respiratory rate variability, user's motion, blood pressure, historical information, and/or user's temperature. In some examples, the control panel 140 can display analysis regarding the user's sleep and/or can provide suggestions to improve the user's sleep.

While the control system 140 can be included in system 199, examples of the disclosure can include any arrangement where the control system 140 is separate and distinct from the system 199. The system 199 can communicate information (e.g., physiological measurements, raw data from the piezo sensors, etc.) to the control system 140 through wired or wireless (e.g., local area network) communication means. In some examples, the control system 140 can include a transceiver to receive information and a controller or processor to process the information for the analyses (e.g., to determine heart rate, heart rate variability, respiratory rate, and respiratory rate variability).

Examples of the disclosure can include information between one or more components being communicated (e.g., using a network) among other components in the system, and information from any combination of components can be used in the analysis of determining one or more of the following: whether one or more criteria are met, whether the blood pressure measurement is successful, whether a measurement in progress should be aborted or annotated, and predictive estimates of physiological information. Examples of the disclosure can further include information being communicated to a central data repository, such as a cloud server.

Examples of the disclosure include using information from one or more signals in determining the user's parameters such as his or her sleep state, blood pressure, heart rate, respiratory rate, etc. In determining a given parameter at a given instance in time, the monitoring system may not include all signals in the analysis. In some examples, the monitoring system may prioritize the signals from the different components based on each signal having a given factor. In some instances, at least two scalers may differ. For example, not all components may be available, so the monitoring system may capable of performing a measurement without signals from the unavailable component(s), which can have a factor equal to 0. As another example, the prioritization may be input by the user or a doctor. The monitoring system may use signals from the sensor(s) with the highest factor (i.e., highest priority) and may use the signals from sensor(s) with the next-highest factor should the highest priority sensor(s) be unsuccessful in or unavailable for determining the user's parameters.

In some examples, the signals can be weighted by multiplying each signal by a respective factor. Some or all of the weighted signals can be added together to reach a resultant summed signal, which can be compared to one or more thresholds to determine whether the measurement criteria are met. In some examples, the weighting can affect the impact the multiplied signal has on beginning a blood pressure measurement.

The prioritization or weighting of the signals may depend on several scalers such as whether a certain pattern is detected, whether a certain magnitude in the signal is detected, and whether certain measurement types have resulted in better signal quality for a given user. For example, in determining the body movement of the user, if the magnitude of the motion signal from the portable device is lower than a certain threshold, the monitoring system may multiply the values from the motion signal from the mat by a higher factor than the factor for the portable device. Alternatively, the portable device can have higher priority than the mat. The monitoring system can measure the motion signal from the portable device first and resort to measuring the motion signal from the mat when the motion signal from the portable device does not meet a certain threshold.

In other examples, the monitoring system can use an algorithm to determine the state or condition of the user, which can drive further decisions such as whether to take a measurement, whether to delay a measurement and/or for how long, whether to label a measurement, etc. The algorithm can be a linear or non-linear algorithm. The algorithm can use (e.g., combine) one or more input values (e.g., signals) to provide one or more outputs. In some instances, the inputs can be signals generated by the sensor(s).

Overview of the Operation of the Monitoring System

Figure 2:
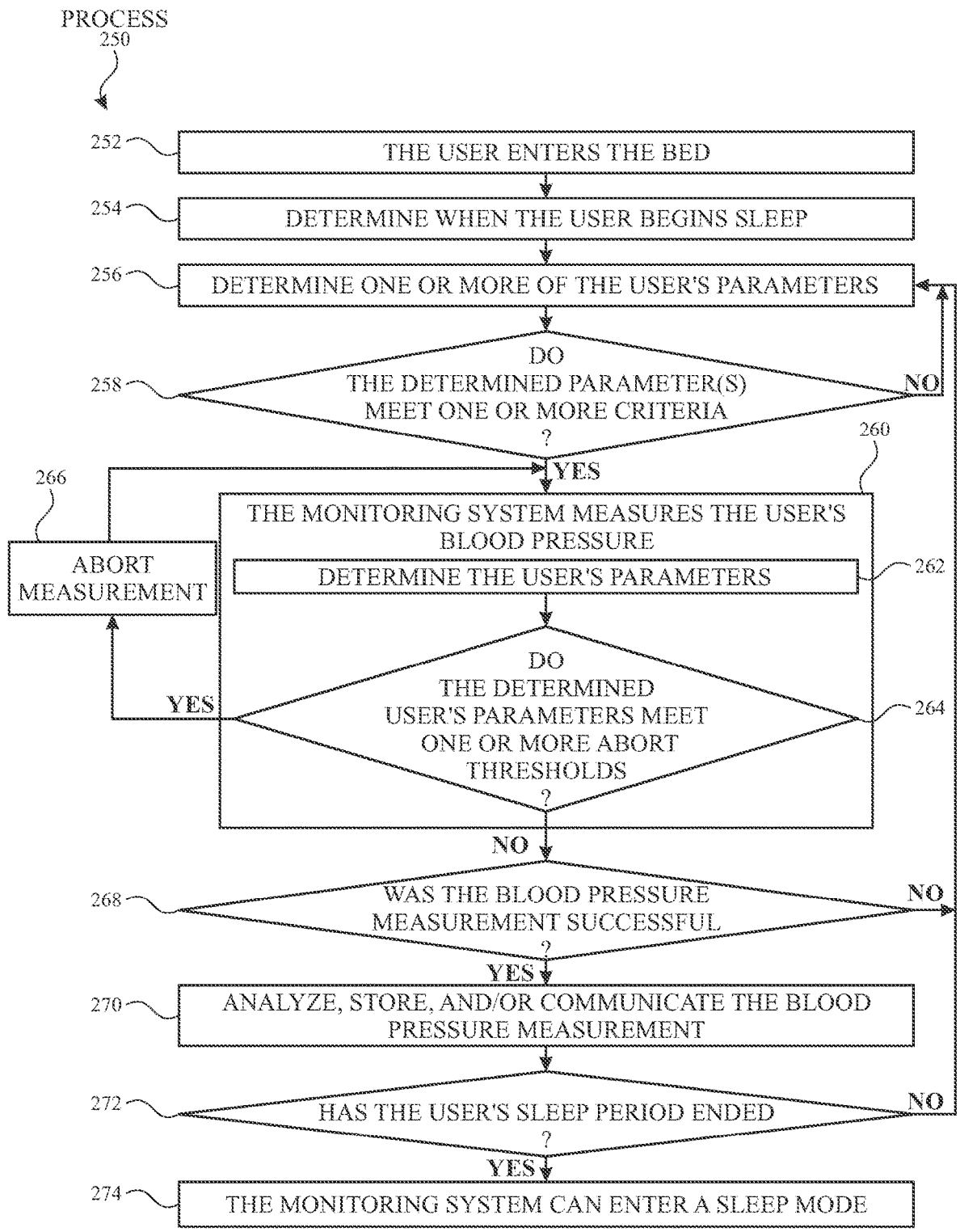
FIG. 2 illustrates a flow chart of an exemplary process of operation of the monitoring system according to examples of the disclosure.

FIG. 2 illustrates a flow chart of an exemplary process of operation of the monitoring system according to examples of the disclosure. Process 250 begins with the user's entering the bed (step 252). In some instances, the user may not be asleep the entire time while in bed, so the monitoring system can determine when the user begins sleep (step 254 of process 250). While asleep, the monitoring system (e.g., system 199 illustrated in FIG. 1) can use one or more components to determine one or more of the user's parameters (step 256 of process 250). The user's parameters may be monitored throughout the course of the user's sleep. The term "sleep period" used throughout this disclosure refers to the period when the user is sleeping over the course of the day and may include multiple sub-periods that are non-consecutive in time. Examples of the disclosure are not limited to the same components being used and are not limited to the same parameters being measured throughout the user's sleep period. As discussed in detail below, the monitoring system can determine the user's parameters at any given instance and dynamically adjust the measurement parameters, criteria, and acquired information based on the user's parameters. The monitoring system can use the user's parameters to determine whether one or more criteria (e.g., sleep state) are met (step 258 of process 250). Once the one or more criteria are met, the monitoring system can measure the user's blood pressure (step 260 of process 250). In some examples, the monitoring system may perform one or more functions, such as a haptic pre-inflation (e.g., a vibration or sound) of the cuff, to check whether the user is in a certain sleep state.

In some examples, the monitoring system can measure the user's parameters during the measurement (step 262 of process 250) and then determine whether the parameters meet one or more thresholds (step 264 of process 250), as discussed further below. If the parameters measured during the blood pressure measurement meet one or more thresholds, then the monitoring system can abort the measurement (step 266 of process 250). Alternatively, instead of aborting the measurement, the measurement can be annotated so that the measurement can be used during data interpretation with certain qualifiers attached. In some examples, the monitoring system can wait until one or more criteria (e.g., a predetermined amount of time) are met before retrying the measurement. If the measurement was not aborted, the monitoring system can determine if the blood pressure measurement was successful (step 268 of process 250).

If the blood pressure measurement was not successful, then the monitoring system can retry the measurement. If the blood pressure measurement was successful, then the blood pressure measurement information can be analyzed, stored in memory, and/or communicated (e.g., to a doctor) (step 270 of process 250). The measurements can continue until the user's sleep period (or sub-period) ends, as determined by the monitoring system (step 272 of process 250). Optionally, the monitoring system can enter into a sleep mode (step 274 of process 250) until the user begins another sleep period. The monitoring system can then return to step 254 to determine when the user begins another sleep period (or sub-period).

Measurement Criteria

As discussed above, the monitoring system can measure the user's blood pressure once one or more criteria are met. The criteria can be pre-determined or can be dynamically adjusted based on previously acquired measurement information. One criterion can include the user's sleep state. The blood pressure measurement can include a step of inflating a cuff that may be wrapped around the user's arm, for example. To minimize the amount of sleep disruption and to enhance the accuracy of the measurement, the monitoring system may wait to take a blood pressure measurement until the user is in a certain sleep state. During the user's certain sleep state, the user is less likely to notice the cuff inflation and his or her blood pressure during this time is more likely to be at a minimum and stable.

Figure 3:
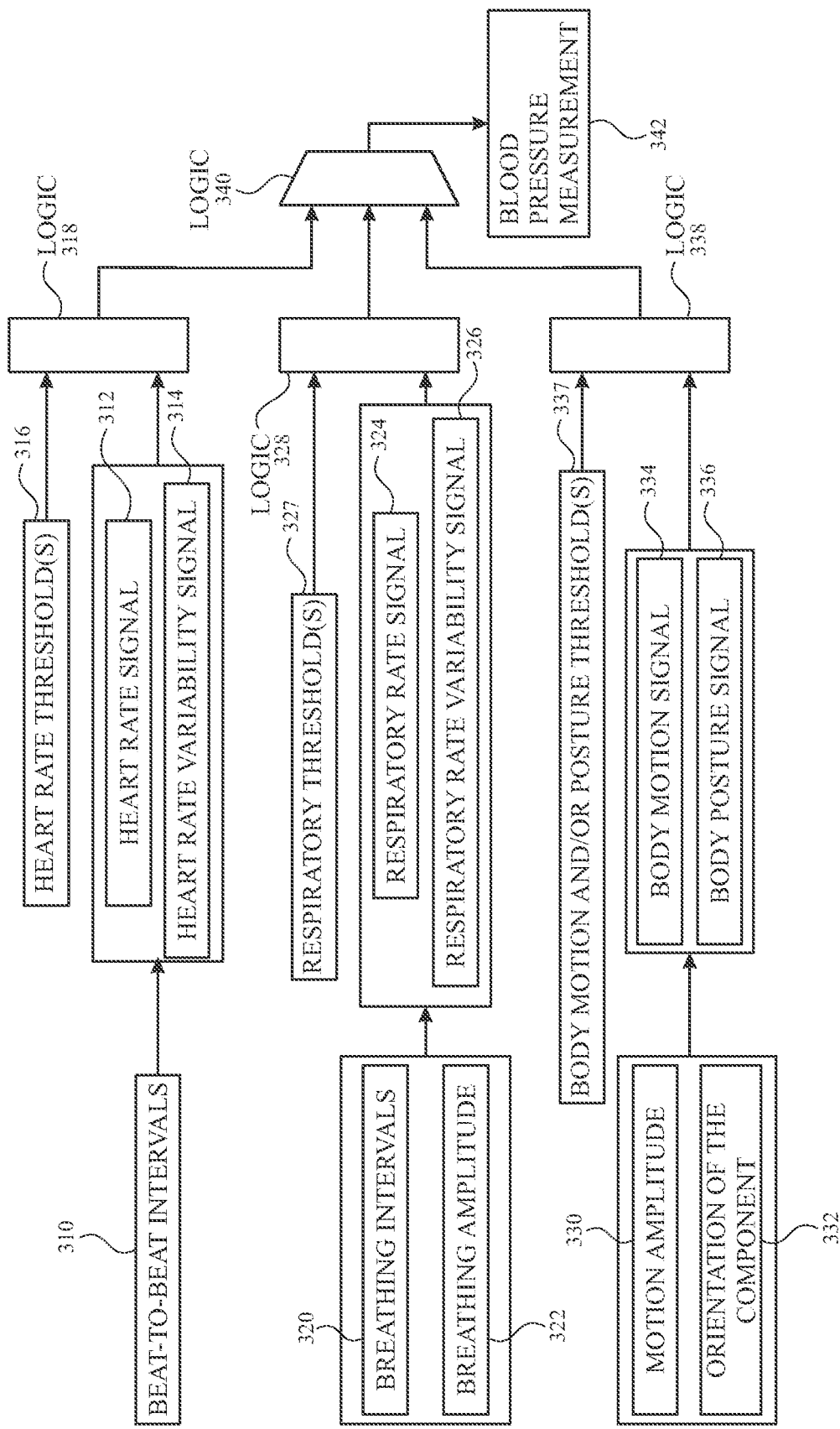
FIG. 3 illustrates a block diagram of exemplary measurement criteria according to examples of the disclosure.

The monitoring system can determine whether the user is in a certain sleep state based on one or more measurement criteria. FIG. 3 illustrates a block diagram of exemplary measurement criteria according to examples of the disclosure. The measurement criteria may be related to physiological parameters such as the user's heart rate, respiration rate, snoring pattern, body movement, body position, body posture, eye movement, or the like. Examples of the disclosure can include using one measurement criterion or multiple measurement criteria. The measurement criteria, as determined by logic 340, may be fixed or may dynamically change based on certain conditions (e.g., whether the battery levels on a component are low, whether a component is unavailable, the success of a measurement, etc.).

One measurement criterion can be associated with the user's heart rate. One or more components (e.g., a PPG or $SpO_2$ sensing unit included in the cuff 112 illustrated in FIGS. 1A-1B) can detect beat-to-beat intervals 310 (measured in time units). In some examples, the measured beat-to-beat intervals can be used to generate heart rate signal(s) 312 and heart rate variability signal(s) 314. The monitoring system can determine whether the heart rate signal 312 and/or heart rate variability signal 314 meet one or more heart rate thresholds 316 (e.g., in step 258 of process 250 illustrated in FIG. 2) using logic 318, for example. If the generated heart rate-related signal(s) meet the criteria, then the monitoring system can perform a blood pressure measurement 342. As one example, one criterion can be the heart rate not changing (e.g., increasing) by more than 5% for a given duration threshold (e.g., 5 minutes). In some examples, the monitoring system can determine whether the measured beat-to-beat intervals 310 themselves meet the criteria.

Another measurement criterion can be associated with the user's breathing. One or more components (e.g., the microphone included in the bedside monitor 110 illustrated in FIG. 1A, the piezo sensors 134 illustrated in FIG. 1A, etc.) can detect the breathing intervals and breathing amplitudes. The measured breathing intervals can be used to generate respiratory rate and respiratory rate variability signals. The measured breathing amplitudes can also be used to generate respiratory variability signals. The monitoring system can determine whether the respiratory rate signal and/or respiratory rate variability signal meet one or more respiratory thresholds (e.g., in step 258 of process 250 illustrated in FIG. 2) using logic 328, for example. If the generated respiratory signal(s) meet the criteria, then the monitoring system can perform a blood pressure measurement. In some examples, the monitoring system can determine whether the measured breathing intervals and/or breathing amplitudes meet the criteria.

Another measurement criterion can be associated with the user's body movement, position, and/or posture of the user. One or more components (e.g., an accelerometer or gyrometer included in the cuff 112 illustrated in FIGS. 1A-1B, piezo sensors 134 included in the mat 102 illustrated in FIG. 1A, an accelerometer included in the portable device 114 illustrated in FIGS. 1A-1B, a radar included in the bedside monitor 110 illustrated in FIG. 1A, etc.) can measure the motion amplitude 330 and/or the orientation of the component 332. The measured motion amplitude 330 can be used to generate body motion signal(s) 334, and the measured orientation of the component can be used to generate body posture signal(s) 336. The monitoring system can determine whether the motion signal(s) 334 and/or body posture signal(s) 336 meet one or more motion or posture thresholds 337 (e.g., in step 258 of process 250 illustrated in FIG. 2) using logic 338, for example. If the generated motion signal(s) 334 and/or body posture signal(s) 336 meet the criteria, then the monitoring system can perform a blood pressure measurement 342. As one example, one criterion can be fewer than two spikes in the acceleration signal during a window lasting a duration threshold (e.g., a two-minute window). In some examples, the monitoring system can determine whether the measured orientation of the component itself meets the criteria.

Certain body postures may be associated with enhanced blood pressure measurement conditions, and the monitoring system may favor (e.g., relax the measurement thresholds) the body postures associated with enhanced blood pressure measurement conditions. For example, more accurate blood pressure measurements can be taken when the user's arms are down (e.g., the hands are located closer to the user's torso), as shown in FIG. 1B. The monitoring system can take the measurements when the user's arms are down and may not take any measurements when the user's arms are up (e.g., located above the user's shoulders). As another example, different blood pressure measurement signals may result when the user is sleeping on his or her back (supine) compared to when the user is sleeping on his or her abdomen (prone). The monitoring system may be configured to perform measurements when the user has the same posture (e.g., only when the user is supine) such that the measurement conditions are consistent among multiple measurements.

In some examples, the monitoring system can determine that the user has a certain posture and include one or more offsets in the measurements to account for such posture. For example, the user may be sleeping on his or her side, which may cause a change (e.g., decrease) in the blood pressure. In some instances, the change in blood pressure may be due to hydrostatic effects. One or more offsets can be included in the measurement, where the offset(s) can be based on the hydrostatic pressure distance. The hydrostatic pressure distance can be the distance from the user's sternum to the middle of the upper portion of the user's arm. In some examples, the offset(s) can be reduced when the user is not sleeping completely (i.e., perpendicular to the bed) on his or her side.

The monitoring system can use patterns for determining whether one or more measurement criteria are met. One example is the user's snoring pattern (e.g., measured by the bedside monitor 110 illustrated in FIGS. 1A-1B). The monitoring system can store pre-determined snoring patterns to be compared to the pattern of the measured noise signals. If the measured pattern matches the pre-determined pattern, then the monitoring system can perform the blood pressure measurement.

Another example is a user-specific blood pressure pattern. For example, the monitoring system may store historical information about the user's blood pressure cycle as a pre-determined pattern. The monitoring system may compare the pre-determined blood pressure pattern to be compared to the pattern of the measured blood pressure signals. Additionally or alternatively, the monitoring system may compare the information as the blood pressure measurements are being performed, and once the trend in the measured blood pressure signals matches, the monitoring system may predict future blood pressure signal values. The monitoring system may also determine when in the blood pressure cycle a measurement for a given sleep period should be taken.

The measurement criteria may, additionally or alternatively, be based on the sleep pattern specific to the user. For example, the monitoring system may use historical information about the user's sleep to generate and store a pre-determined sleep pattern, later to be used for determining whether the measurement criteria have been met.

Examples of the disclosure can include waiting until multiple criteria are met before taking a blood pressure measurement. For example, the monitoring system may wait until the user's heart rate meets the heart rate threshold(s). The monitoring system may also wait until the user's body motion signal meets the body motion threshold for a given duration threshold (e.g., 5 minutes). When the heart rate threshold, body motion threshold, and duration threshold are met, then the monitoring system may take a blood pressure measurement. In some examples, the monitoring system may take the blood pressure measurement while the criteria are not met, but may ignore or discard the signals, or alternatively annotate or flag the signals if the criteria are not met.

Non blood pressure examples of the disclosure include measuring other metrics related to cardiovascular health during various user states, such as a sleep state, only when certain criteria are met. For example, the brachial artery pressure waveform can be measured by inflating a blood pressure cuff to a level between diastolic blood pressure (DBP) and systolic blood pressure (SBP) and holding it at that level for a period of time. From the waveform shape, it may be possible to perform analyses such as pulse wave analysis (PWA) to infer information on arterial stiffness, for example.

Non-sleep examples of the disclosure can use other criteria. For example, after exercise, the monitoring system may wait a specified period of time (a rest period) and/or until the user's heart rate meets the heart rate threshold(s). The monitoring system may also wait until the user's body motion signal meets the body motion threshold for a given duration threshold (e.g., 5 minutes), indicating exercise has ceased, or that a certain posture is detected, such as sitting in a chair. When the various criteria have been met, the monitoring system may take a physiological measurement such as a blood pressure measurement. In some examples, the monitoring system may take the physiological measurement even while the criteria are not met, but may ignore or discard the signals, or alternatively annotate or flag the signals with information such as activity levels leading up to the measurement, or alert the user.

Dynamic Adjustment of the Measurement Thresholds

The measurement thresholds can be dynamically adjusted based on one or more scalers including, but not limited to how much time has passed since the last successful measurement, what percentage of the time has the user spent in or not in a certain sleep state, and how much time remains until the end of the sleep period. The dynamic adjustment can occur during the sleep period or in-between sleep periods.

Figure 4:
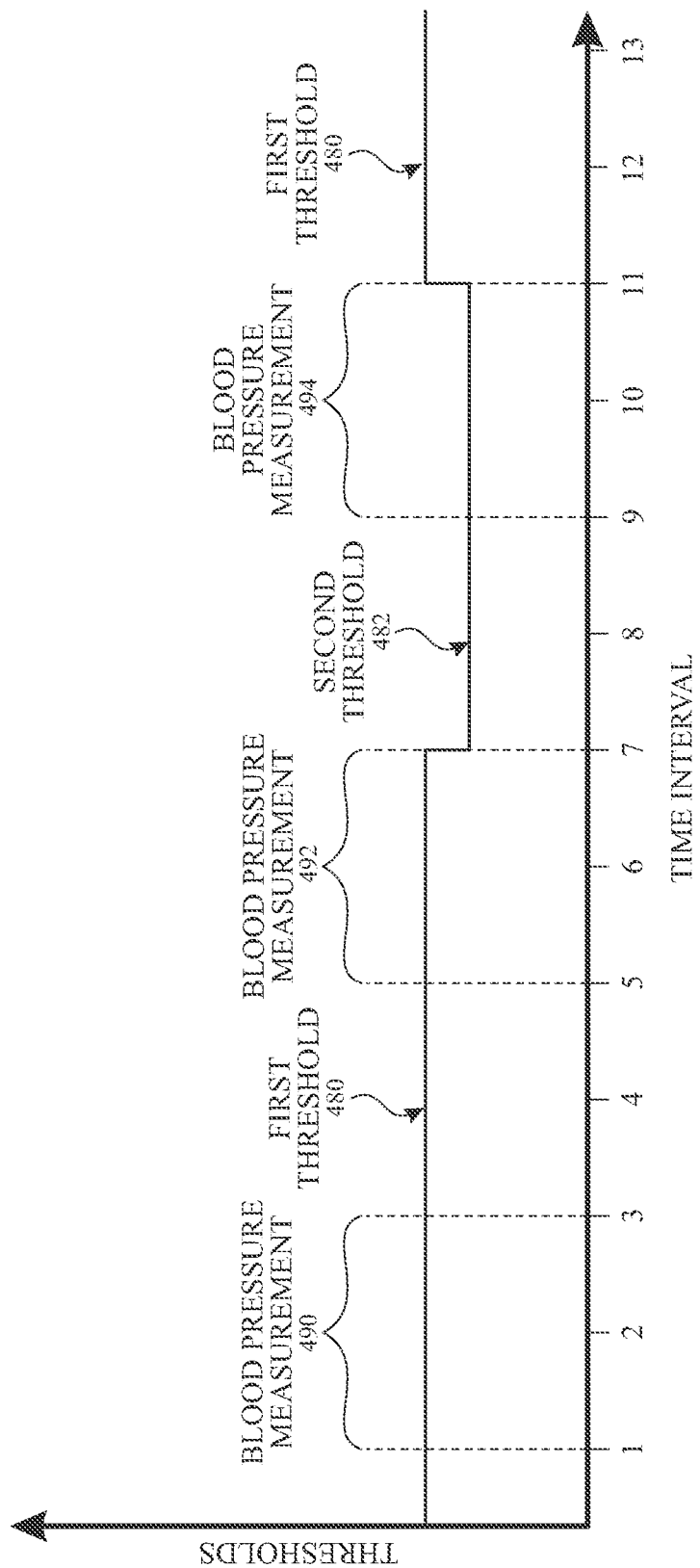
FIG. 4 illustrates an exemplary time plot showing the dynamic adjustment of the measurement thresholds according to examples of the disclosure.

For example, the measurement thresholds can be decreased as the duration (or number of attempts) since the last successful measurement becomes greater. FIG. 4 illustrates an exemplary time plot showing the dynamic adjustment of the measurement thresholds according to examples of the disclosure. The threshold can be set to a first threshold 480. During time intervals 1-3, a blood pressure measurement 490 can be taken (e.g., due to one or more criteria being met). The blood pressure measurement 490 may be unsuccessful (e.g., due to the measurement being aborted or annotated) as measured against a success threshold. During time intervals 5-7, another blood pressure measurement 492 may be taken. The blood pressure measurement 492 may also be unsuccessful (e.g., due to too much noise in the measurement, improper inflation of the cuff, etc.). The monitoring system may then dynamically adjust the measurement threshold by lowering it to a second threshold 482. The blood pressure measurement 494 can be taken once the lower second threshold 482 has been met. The second lower threshold 482 may be, e.g., indicative of the user's body movement during the measurement. In some instances, the threshold may be changed after a successful measurement has been taken. For example, the threshold may be changed back to the first threshold 480. In some examples, the monitoring system may change the threshold in a step-wise fashion until a successful measurement has been taken. In this manner, the monitoring system can ensure that a sufficient number of measurements can be taken over the course of the sleep period.

As another example, the measurement thresholds can be increased if the user has spent a large percentage (e.g., 50%) of the sleep period in the certain sleep state. Repeated measurements of the user being in the certain sleep state may not enhance the accuracy of the measurement and/or may not add any more pertinent information. Increasing the measurement threshold may decrease the number of measurements taken, thereby reducing the likelihood of disrupting the user's sleep and reducing the amount of power consumed.

If the user has not spent a certain percentage of the sleep period in the certain sleep state, the measurements threshold may be relaxed to increase the number of measurements. In some examples, the monitoring system may look at the user's percentage in the certain sleep state and/or number of measurements over the course of multiple sleep periods (e.g., days) to determine whether and how much to relax the measurements thresholds.

In some examples, the monitoring system can count the number of successful measurements taken over the course of the sleep period. If the number of successful measurements is less than a certain success threshold, then the monitoring system may take a measurement as the monitoring system determines the user is beginning to wake up (e.g., by observing a gradual increase in heart rate). The monitoring system can decrease the success threshold as time approaches closer to the user's typical wake up time (i.e., end of the sleep period). In other words, in some examples, the number of successful measurements needed to constitute a successful set of measurements (as determined by the measurement threshold) can be reduced as the remaining time available for measurement decreases.

Dynamic Adjustment of the Measurement Parameters

In some examples, the measurement parameters for one or more components may be adjusted. In adjusting the measurement parameters, signals from one component may be used to provide information for adjusting the measurement parameters for another component. For example, the accelerometer in the portable device (e.g., a wearable or handheld electronic device) can determine a certain pattern of the user's body movement, where valleys in the pattern may coincide with a given sleep state of the user. The signals from the accelerometer can be used to adjust the sensitivity of the piezoelectric sensors on the mat. As another example, the signals from the optical sensors in the cuff may be used to cancel noise in the signals from the optical sensors in the portable device.

As yet another example, the systolic blood pressure can decrease during inhalation and increase during exhalation. Depending on the respiration phase (e.g., measured by the radar included in the bedside monitor) relative to the pressure ramp on the cuff (e.g., measured by the pressure sensors included in the cuff), the estimated blood pressure can fluctuate. The pressure ramp on the cuff can be controlled such that blood pressure measurements are taken only during a certain period (e.g., inhalation period), thereby enhancing the blood pressure measurement. In some examples, the blood pressure measurement signal (e.g., the oscillometric pressure waveform) can be considered only during inhalation.

Aborting or Annotating the Measurements

In some instances, the user's parameters before the measurement is taken may meet the criteria, but the parameters may change during the measurements. Changes in the parameters during the measurement may lead to inaccurate measurements and/or analyses. For example, during the measurement, the user may move excessively (i.e., the body movement is greater than a body motion-related abort threshold) or the user may have an unusual breathing pattern (i.e., the respiratory rate variability may be greater than a respiratory rate-related abort threshold). In some examples, the measurement may continue despite the changed parameters and the information may be discarded or ignored. In other examples, the measurement can be aborted. In still other examples, the measurements can continue to completion, with annotations added to the captured measurements to describe the measurement conditions. During the measurements, one or more sensors may be measuring the user's parameters, and the monitoring can check whether the parameters meet one or more abort criteria. If the parameters meet the abort criteria, then the one or more components can deactivate, or the logic may discard the acquired signals. For example, if the user changes his or her body position from a favorable position to a non-favorable position during the measurement, the monitoring system would detect the change in position, and the cuff (e.g., cuff 112 illustrated in FIGS. 1A-1B) can deflate.

As another example, the monitoring system may detect a sudden spike in the user's blood pressure and/or the user's heart rate. Instead of continuing with the blood pressure measurement, the monitoring system may abort the measurement. The monitoring system may then wait until the user's blood pressure and/or heart rate has returned to the level prior to the sudden spike. Alternatively, the monitoring system may wait a certain amount of time before retrying the measurement.

Figure 5:
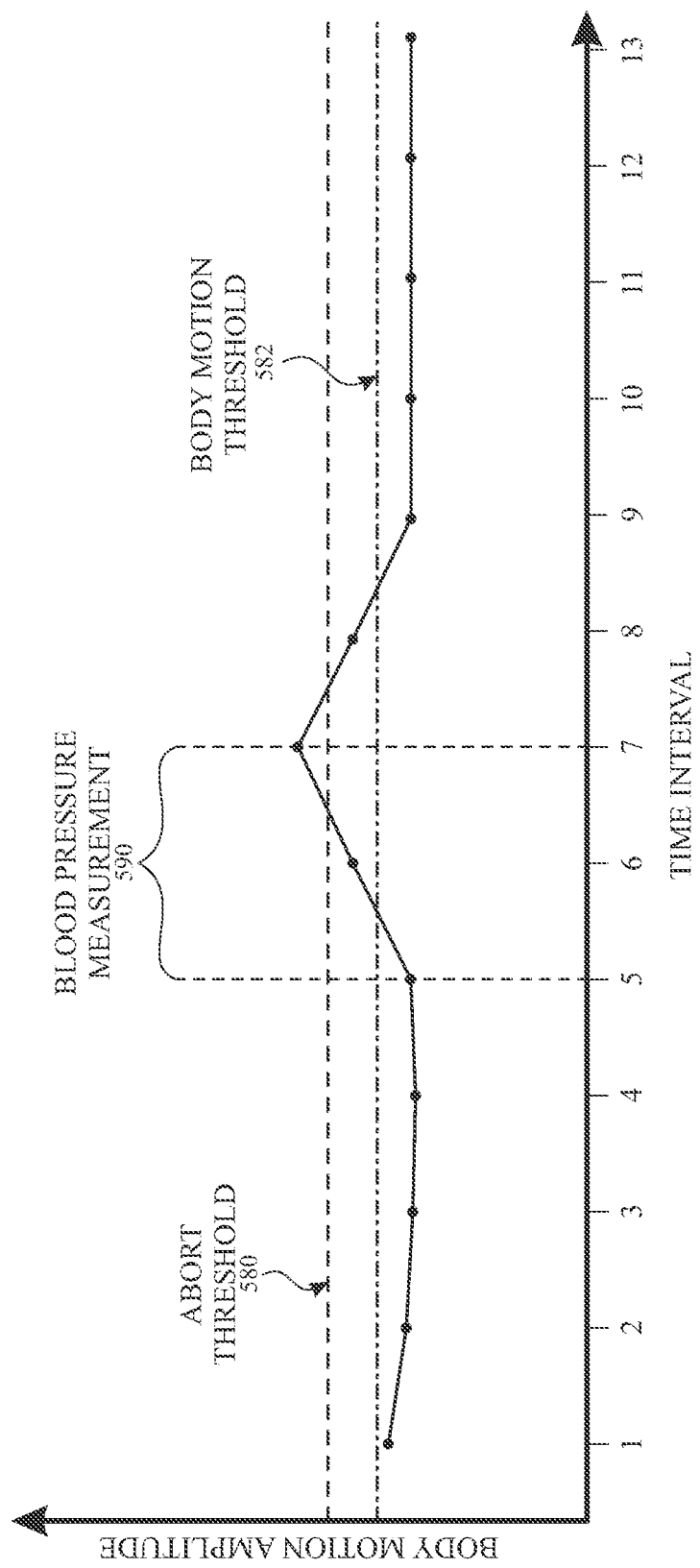
FIG. 5 illustrates an exemplary time plot showing a blood pressure measurement being aborted during the measurement according to examples of the disclosure.

FIG. 5 illustrates an exemplary time plot showing a blood pressure measurement being aborted during the measurement according to examples of the disclosure. The monitoring system can have two or more thresholds (as discussed above): an abort threshold 580 and a criterion threshold (e.g., body motion threshold 582). During the time intervals 1-5, the body motion amplitude may meet the body motion threshold 582 for a given duration. At the beginning of time interval 5, the body motion amplitude may remain below the body motion threshold 582, so the blood pressure measurement 590 may be begin. At the beginning of time interval 6, the body motion amplitude may increase and be greater than the body motion threshold 582. In some examples, the abort threshold 580 may be greater than the body motion threshold 582, as illustrated in the figure. In other examples, the body motion threshold 582 may be the same as the abort threshold. When the body motion amplitude is greater than the abort threshold 580, the blood pressure measurement 590 may abort, as shown in the figure. The monitoring system may discard the measurement, store the instance, adjust one or more measurement parameters, and/or adjust one or more measurement criteria.

A method for monitoring a physiological state of a user is disclosed. The method comprises: measuring one or more first user parameters using one or more first sensors; determining a state of the user and an estimated start of a period during which the user is in the determined state based on the measured one or more first user parameters; determining whether the state of the user or the one or more first user parameters meets one or more first criteria; in accordance with the determined state of the user or the one or more first user parameters meeting the one or more first criteria: initiating a physiological measurement, during the physiological measurement, measuring one or more second user parameters using one or more second sensors, determining whether the measured one or more second user parameters meets one or more second criteria, in accordance with the measured one or more second user parameters not meeting the one or more second criteria: completing the physiological measurement, and one or more of analyzing, storing, and communicating the physiological measurement; and continuing the monitoring until the period ends. Additionally or alternatively, in some examples, the method further comprises: in accordance with the measured one or more second user parameters meeting the one or more second criteria: performing one of aborting the physiological measurement and annotating the physiological measurement, waiting a pre-determined amount of time, and repeating the physiological measurement after the pre-determined amount of time has elapsed. Additionally or alternatively, in some examples, the one or more first user parameters include beat-to-beat intervals, the determination of the state of the user includes generating one or more heart rate signals, one or more heart rate variability signals, or both from the beat-to-beat intervals, and the determination of whether the state of the user meets the one or more criteria includes determining whether the one or more heart rate signals, the one or more heart rate variability signals, or both meet one or more heart rate thresholds. Additionally or alternatively, in some examples, the one or more heart rate signals, the one or more heart rate variability signals, or both are generated using signals from a cuff and a mat. Additionally or alternatively, in some examples, the one or more first user parameters include breathing intervals, breathing amplitudes, or both, the determination of the state of the user includes generating one or more respiratory rate signals, one or more heart rate variability signals, or both from the breathing intervals, the breathing amplitudes, or both, and the determination of whether the state of the user meets the one or more criteria includes determining whether the one or more respiratory rate signals, the one or more heart rate variability signals, or both meet one or more respiratory thresholds. Additionally or alternatively, in some examples, the one or more first user parameters includes one or more of a body movement, a body position, and a body posture of the user, the determination of the state of the user includes generating body motion signals, body posture signals, or both, and the determination of whether the state of the user meets the one or more criteria includes determining whether the body motion signals, the body posture signals, or both meet one or more motion or posture thresholds. Additionally or alternatively, in some examples, the one or more first sensors are included in a cuff. Additionally or alternatively, in some examples, the at least one sensor is included in both the one or more first sensors and the one or more second sensors. Additionally or alternatively, in some examples, the one or more first user parameters include a body posture of the user and the one or more criteria include the body posture of the user being the same. Additionally or alternatively, in some examples, the method further comprises: dynamically adjusting one or more thresholds associated with the one or more criteria based on one or more of a number of successful measurements, a percentage of time in a certain sleep state, and an amount of time until the period ends. Additionally or alternatively, in some examples, the method further comprises: decreasing one or more thresholds associated with the one or more criteria when a duration since a last successful measurement is greater than a predetermined duration. Additionally or alternatively, in some examples, the method further comprises: predicting that the user will switch to a different state; and initiating the physiological measurement in response to the prediction. Additionally or alternatively, in some examples, the method further comprises: receiving one or more signals from the one or more first sensors; determining one or more scalers associated with the one or more first sensors, wherein at least two of the one or more scalers are different, wherein the measurement of the one or more first user parameters using the one or more first sensors includes: measuring the one or more first user parameters using the first sensor having a highest scaler; determining whether the measurement from the first sensor having the highest scaler was successful; and in accordance with the measurement not being successful, measuring the one or more first user parameters using the first sensor having a next highest scaler. Additionally or alternatively, in some examples, the method further comprises: receiving one or more signals from the one or more first sensors; combining the one or more signals using an algorithm to produce one or more outputs; wherein the determination of whether the state of the user or the one or more first user parameters meet the one or more criteria is based on the one or more outputs. Additionally or alternatively, in some examples, the initiation of the physiological measurement includes inflating a cuff to occlude blood flow in the user. Additionally or alternatively, in some examples, the method further comprises: prior to initiating the physiological measurement, inflating the cuff, and determining whether the user is in a given sleep state, wherein the completion of the physiological measurement is in accordance with the determination that the user is in the given state.

A physiological monitoring system is disclosed. The physiological monitoring system comprises: one or more sensors included in one or more components, the one or more sensors configured to measure one or more user parameters; a cuff configured to measure a user's physiology when one or more user states meets one or more criteria, wherein the cuff includes one or more motion sensors configured to measure one or more motion signals, and the one or more user parameters includes information from the one or more motion signals; and a control system configured to determine the one or more user states based on the one or more user parameters. Additionally or alternatively, in some examples, the cuff further includes one or more optical sensors to measure the one or more user parameters. Additionally or alternatively, in some examples, the one or more components include one or more of a portable electronic device, a bedside monitor, a camera, and a head device. Additionally or alternatively, in some examples, the one or more components includes a mat including one or more additional motion sensors configured to measure one or more additional motion signals, and the one or more user parameters includes information from the one or more additional motion signals.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. A method for monitoring a physiological state of a user, the method comprising:

measuring one or more first user parameters using one or more first sensors included in a cuff;

determining a state of the user and an estimated start of a period during which the user is in the determined state based on the measured one or more first user parameters;

determining the state of the user or the one or more first user parameters meet one or more first criteria;

in accordance with the determined state of the user or the one or more first user parameters meeting the one or more first criteria, initiating a physiological measurement of the user using one or more second sensors that are different from the one or more first sensors;

during the physiological measurement, measuring a first set of one or more second user parameters using one or more third sensors that are different from the one or more second sensors, the one or more second user parameters being different from physiological parameters measured as part of the physiological measurement;

determining the first set of the one or more second user parameters do not meet one or more second criteria;

in accordance with the first set of the one or more second user parameters not meeting the one or more second criteria:

adjusting the one or more second criteria; and measuring a second set of the one or more second user parameters using the one or more third sensors;

determining the second set of the one or more second user parameters meet the adjusted one or more second criteria;

in accordance with the second set of the one or more second user parameters meeting the adjusted one or more second criteria:

completing the physiological measurement, and one or more of: analyzing, storing, and communicating the physiological measurement.

2. The method of claim 1, the method further comprising:
in accordance with the second set of the one or more second user parameters not meeting the adjusted one or more second criteria:
performing one of:
aborting the physiological measurement and annotating the physiological measurement,
waiting a pre-determined amount of time, and
repeating the physiological measurement after the pre-determined amount of time has elapsed.

3. The method of claim 1, wherein:
the one or more first user parameters include beat-to-beat intervals,
the determination of the state of the user includes generating one or more heart rate signals, one or more heart rate variability signals, or both from the beat-to-beat intervals, and
the determination that the state of the user meets the one or more first criteria includes determining the one or more heart rate signals, the one or more heart rate variability signals, or both meet one or more heart rate thresholds.

4. The method of claim 3, wherein the one or more heart rate signals, the one or more heart rate variability signals, or both are generated using signals from the cuff, a mat, or a combination thereof.

5. The method of claim 1, further comprising measuring breathing intervals, breathing amplitudes or both, wherein:
the determination of the state of the user includes generating one or more respiratory rate signals, one or more heart rate variability signals, or both from the breathing intervals, the breathing amplitudes, or both, and
the determination that the state of the user meets the one or more first criteria includes determining the one or more respiratory rate signals, the one or more heart rate variability signals, or both meet one or more respiratory thresholds.

6. The method of claim 1, wherein:
the one or more first user parameters includes one or more of: a body movement, a body position, and a body posture of the user,
the determination of the state of the user includes generating body motion signals, body posture signals, or both, and
the determination that the state of the user meets the one or more first criteria includes determining the body motion signals, the body posture signals, or both meet one or more motion or posture thresholds.

7. The method of claim 1, wherein:
the one or more first sensors comprises multiple sensors;
the one or more second sensors comprises multiple sensors; and
at least one same sensor is included in both the one or more first sensors and the one or more second sensors.

8. The method of claim 1, wherein the one or more first user parameters include a body posture of the user, and the one or more criteria corresponds to a predetermined body posture of the user.

9. The method of claim 1, further comprising:
dynamically adjusting one or more thresholds associated with the one or more second criteria based on one or more of: a number of successful measurements, a percentage of time in a certain sleep state, and an amount of time until the period ends.

10. The method of claim 9, further comprising:
decreasing one or more thresholds associated with the one or more second criteria when a duration since a last successful measurement is greater than a predetermined duration.

11. The method of claim 1, further comprising:
predicting that the user will switch to a different state; and
initiating the physiological measurement in response to the prediction.

12. The method of claim 1, further comprising:
receiving one or more signals from the one or more first sensors;
determining one or more scalers associated with the one or more first sensors, wherein at least two of the one or more scalers are different,
wherein the measurement of the one or more first user parameters using the one or more first sensors includes:
measuring the one or more first user parameters using a sensor of the one or more first sensors having a highest scaler;
determining the measurement from the sensor having the highest scaler was successful; and
in accordance with the measurement not being successful, measuring the one or more first user parameters using a sensor of the one or more first sensors having a next highest scaler.

13. The method of claim 1, further comprising:
receiving one or more signals from the one or more first sensors;
combining the one or more signals using an algorithm to produce one or more outputs;
wherein the determination that the state of the user or the one or more first user parameters meet the one or more first criteria is based on the one or more outputs.

14. The method of claim 1, wherein the initiation of the physiological measurement includes inflating the cuff to occlude blood flow in the user.

15. The method of claim 14, further comprising:
prior to initiating the physiological measurement, inflating the cuff and determining the user is in a given sleep state,
wherein the completion of the physiological measurement is in accordance with the determination that the user is in the given state.

16. A physiological monitoring system comprising:
one or more first sensors operable to monitor one or more first user parameters;
a cuff comprising one or more second sensors operable to measure a physiological parameter of a user;
one or more third sensors, different from the one or more second sensors and operable to measure one or more second user parameters that are different from the physiological parameter; and
a processing unit operable to:
determine a state of the user and an estimated start period during which the user is in the determined state based on the measured one or more first user parameters;
in accordance with the state of the user meeting a first criteria, initiate a physiological measurement of the user using the one or more second sensors;
during the physiological measurement, measure a first set of the one or more second user parameters using the one or more third sensors; and
in accordance with the first set of the one or more second user parameters not meeting a second criteria:

adjusting the one or more second criteria; and
measuring a second set of the one or more second user parameters using the one or more third sensors; and
in accordance with the second set of the one or more second user parameters meeting the adjusted one or more second criteria:
complete the physiological measurement; and
causing display of the physiological measurement on a portable device.

17. The physiological monitoring system of claim 16, wherein the one or more second sensors comprise one or more optical sensors.

18. The physiological monitoring system of claim 16, wherein the one or more first sensors comprise one or more of: a portable electronic device, a bedside monitor, a camera, and a head device.

19. The physiological monitoring system of claim 16, wherein:
the one or more first sensors comprise a mat including one or more motion sensors configured to measure motion signals; and
the one or more user parameters include information from the measured motion signals.

20. The physiological monitoring system of claim 16, wherein:
the processing unit is operable to abort the measurement of the user's physiological parameter when the measured one or more second user parameters meet the second criteria during the measurement.

* * * * *